(12) United States Patent
Burrell et al.

(10) Patent No.: US 6,719,987 B2
(45) Date of Patent: Apr. 13, 2004

(54) ANTIMICROBIAL BIOABSORBABLE MATERIALS

(75) Inventors: Robert Edward Burrell, Sherwood Park (CA); Hua Qing Yin, Sherwood Park (CA); Stojan Djokic, Emdonton (CA); Rita Johanna Mary Langford, Edmonton (CA)

(73) Assignee: Nucryst Pharmaceuticals Corp., Alberta (CA)

( * ) Notice: Subject to any disclaimer, the term of this patent is extended or adjusted under 35 U.S.C. 154(b) by 0 days.

(21) Appl. No.: 09/835,859

(22) Filed: Apr. 16, 2001

(65) Prior Publication Data

US 2001/0055622 A1 Dec. 27, 2001

Related U.S. Application Data

(60) Provisional application No. 60/197,959, filed on Apr. 16, 2001.

(51) Int. Cl.$^7$ .......................... A61F 13/00; A01N 25/00
(52) U.S. Cl. ...................................... 424/405; 424/422
(58) Field of Search ............................... 424/422, 423, 424/405

(56) References Cited

U.S. PATENT DOCUMENTS

| | | |
|---|---|---|
| 3,757,786 A | 9/1973 | Smith ...................... 128/335.5 |
| 3,800,792 A | 4/1974 | McKnight et al. .......... 128/156 |
| 3,918,446 A | 11/1975 | Buttaravoli |
| 4,059,105 A | 11/1977 | Cutruzzula et al. |
| 4,167,045 A | 9/1979 | Sawyer ........................... 3/1.4 |
| 4,324,237 A | 4/1982 | Buttaravoli |
| 4,355,636 A | 10/1982 | Oetjen et al. |
| 4,476,590 A | 10/1984 | Scales et al. .................. 3/1.91 |
| 4,581,028 A | 4/1986 | Fox, Jr. et al. ................. 623/2 |
| 4,596,556 A | 6/1986 | Morrow et al. |
| 4,633,863 A | 1/1987 | Filips et al. |
| 4,749,572 A | 6/1988 | Ahari |
| 4,790,824 A | 12/1988 | Morrow et al. |
| 4,803,066 A | 2/1989 | Edwards |
| 4,828,832 A | 5/1989 | De Cuellar et al. .......... 424/618 |
| 4,847,049 A | 7/1989 | Yamamoto .................... 422/24 |
| 4,952,411 A | 8/1990 | Fox, Jr. et al. |
| 4,960,413 A | 10/1990 | Sagar et al. ................. 604/289 |
| 5,019,096 A | 5/1991 | Fox, Jr. et al. ................. 623/1 |
| 5,064,413 A | 11/1991 | McKinnon et al. |
| 5,122,418 A | 6/1992 | Nakane et al. |
| 5,143,717 A | 9/1992 | Davis |
| 5,236,421 A | 8/1993 | Becher |
| 5,270,358 A | 12/1993 | Asmus |
| 5,312,335 A | 5/1994 | McKinnon et al. |

(List continued on next page.)

FOREIGN PATENT DOCUMENTS

| | | |
|---|---|---|
| CA | 2242033 | 1/1999 |
| CN | 1082645 | 2/1994 |
| CN | 1241662 | 1/2000 |
| CN | 1262093 | 8/2000 |
| CN | 1279222 | 1/2001 |

(List continued on next page.)

OTHER PUBLICATIONS

Shigemasa Y. and Minami, S. 1995. Applications of chitin and chitosan for biomaterials. Biotechnology and Genetic Engineering Reviews 13: 383–420.

(List continued on next page.)

*Primary Examiner*—Thurman K. Page
*Assistant Examiner*—S. Howard
(74) *Attorney, Agent, or Firm*—Fish & Richardson P.C.

(57) ABSTRACT

The invention provides bioabsorbable materials with antimicrobial coatings or powders which provide an effective and sustainable antimicrobial effect. Specifically, this invention provides bioabsorbable materials comprising a bioabsorbable substrate associated with one or more antimicrobial metals being in a crystalline form characterized by sufficient atomic disorder, such that the bioabsorbable material in contact with an alcohol or water based electrolyte, releases atoms, ion, molecules, or clusters of at least one antimicrobial metal at a concentration sufficient to provide an antimicrobial effect. The one or more antimicrobial metals do not interfere with the bioabsorption of the bioabsorbable material, and do not leave behind particulates larger than 2 μm, as measured 24 hours after the bioabsorbable material has disappeared. Most preferably, the particulate sizing from the coating or powder is sub-micron that is less than about 1 μm, as measured 24 hours after the bioabsorbable material has disappeared. Particulates are thus sized to avoid deleterious immune responses or toxic effects. Such antimicrobial metals are in the form of a continuous or discontinuous coating, a powder, or a coating on a bioabsorbable powder. The antimicrobial coating is thin, preferably less than 900 nm or more preferably less than 500 nm, and very fine grained, with a grain size (crystallite size) of preferably less than 100 nm, more preferably less than 40 nm, and most preferably less than 20 nm. The antimicrobial coating is formed of an antimicrobial metal, which is overall crystalline, but which is created with atomic disorder, and preferably also having either or both of a) a high oxygen content, as evidenced by a rest potential greater than about 225 mV, more preferably greater than about 250 mV, in 0.15 M $Na_2CO_3$ against a SCE (standard calomel electrode), or b) discontinuity in the coating. The antimicrobial metal associated with the bioabsorbable substrate may also be in the form of a powder, having a particle size of less than 100 μm, or preferably less than 40 μm, and with a grain size (crystallite size) of preferably less than 100 nm, more preferably less than 40 nm, and most preferably less than 20 nm. Such powders may be prepared as a coating preferably of the above thickness, onto powdered biocompatible and bioabsorbable substrates; as a nanocrystalline coating and converted into a powder; or as a powder of the antimicrobial metal which is cold worked to impart atomic disorder. Methods of preparing the above antimicrobial bioabsorbable materials are thus also provided.

28 Claims, No Drawings

U.S. PATENT DOCUMENTS

| | | | |
|---|---|---|---|
| D349,958 S | 8/1994 | Hollis et al. | |
| 5,369,155 A | 11/1994 | Asmus | |
| 5,372,589 A | 12/1994 | Davis | |
| 5,383,851 A | 1/1995 | McKinnon, Jr. et al. | |
| 5,399,163 A | 3/1995 | Peterson et al. | |
| 5,423,859 A | 6/1995 | Koyfman et al. | 606/228 |
| 5,454,886 A | 10/1995 | Burrell et al. | 148/565 |
| 5,454,889 A | 10/1995 | McNicol et al. | |
| 5,457,015 A | 10/1995 | Boston | 430/529 |
| 5,520,639 A | 5/1996 | Peterson et al. | |
| 5,534,288 A | 7/1996 | Gruskin et al. | 427/2.31 |
| 5,563,132 A | 10/1996 | Bodaness | |
| 5,569,207 A | 10/1996 | Gisselberg et al. | |
| 5,578,073 A | 11/1996 | Haimovich et al. | 623/1 |
| 5,631,066 A | 5/1997 | O'Brien | 428/195 |
| 5,681,575 A * | 10/1997 | Burrell et al. | 424/423 |
| 5,697,976 A | 12/1997 | Chesterfield et al. | 623/11 |
| 5,744,151 A | 4/1998 | Capelli | |
| 5,770,255 A | 6/1998 | Burrell et al. | 427/2.1 |
| 5,792,793 A | 8/1998 | Oda et al. | |
| 5,895,419 A | 4/1999 | Tweden et al. | 623/2 |
| 5,899,880 A | 5/1999 | Bellhouse et al. | |
| 5,945,032 A | 8/1999 | Breitenbach et al. | |
| 5,981,822 A | 11/1999 | Addison | |
| 6,010,478 A | 1/2000 | Bellhouse et al. | |
| 6,013,050 A | 1/2000 | Bellhouse et al. | |
| 6,022,547 A | 2/2000 | Herb et al. | |
| 6,071,541 A | 6/2000 | Murad | |
| 6,071,543 A | 6/2000 | Thornfeldt | |
| 6,096,002 A | 8/2000 | Landau | |
| 6,123,925 A | 9/2000 | Barry et al. | |
| 6,126,931 A | 10/2000 | Sawan et al. | |
| 6,165,440 A | 12/2000 | Esenaliev | |
| 6,187,290 B1 | 2/2001 | Gilchrist et al. | |
| 6,197,351 B1 | 3/2001 | Neuwirth | |
| 6,201,164 B1 | 3/2001 | Wulff et al. | |
| 6,224,898 B1 | 5/2001 | Balogh et al. | |
| 6,258,385 B1 | 7/2001 | Antelman | |
| 6,277,169 B1 | 8/2001 | Hampden-Smith et al. | |
| 6,294,186 B1 | 9/2001 | Beerse et al. | 424/405 |
| 6,365,130 B1 | 4/2002 | Barry et al. | |
| 2001/0010016 A1 | 7/2001 | Modak et al. | |
| 2002/0001628 A1 | 1/2002 | Ito | |
| 2002/0016585 A1 | 2/2002 | Sachse | |
| 2002/0025344 A1 | 2/2002 | Newman et al. | |
| 2002/0045049 A1 | 4/2002 | Madsen | |

FOREIGN PATENT DOCUMENTS

| | | | |
|---|---|---|---|
| CN | 1291666 | 4/2001 | |
| CN | 1291667 | 4/2001 | |
| CN | 1306117 | 8/2001 | |
| CN | 1322474 | 11/2001 | |
| CN | 1322874 | 11/2001 | |
| CN | 1328819 | 1/2002 | |
| CN | 1328827 | 1/2002 | |
| DE | 2748882 | 5/1979 | |
| DE | 3807944 | 9/1989 | |
| DE | 195 41 735 A1 | 5/1997 | |
| EP | 0 136 768 | 4/1985 | |
| EP | 0 254 413 | 1/1988 | |
| EP | 0 356 060 | 7/1989 | A61L/25/00 |
| EP | 0 355 009 | 2/1990 | |
| EP | 0 378 147 | 7/1990 | |
| EP | 0 599 188 | 6/1994 | |
| EP | 0 681 841 A1 | 11/1995 | |
| EP | 0780138 | 6/1997 | |
| EP | 1 159 972 | 12/2001 | |
| GB | 420052 | 11/1934 | |
| GB | 427106 | 4/1935 | |
| GB | 965010 | 7/1964 | |
| GB | 1270410 | 4/1972 | |
| GB | 2 073 024 A * | 10/1981 | |
| GB | 2 140 684 | 12/1984 | |
| HU | 980078 A | 9/1999 | |
| IT | 022309 | 12/1990 | |
| JP | 60-21912 | 2/1985 | |
| JP | 04244029 A | 9/1992 | |
| JP | 11 060493 A | 3/1999 | |
| JP | 11 116488 A | 4/1999 | |
| JP | 11 124335 A | 5/1999 | |
| JP | 2000327578 | 11/2000 | |
| WO | 87/07251 | 12/1987 | |
| WO | WO 89/09054 | 10/1989 | |
| WO | WO 92/13491 | 8/1992 | A61B/17/064 |
| WO | WO 93/23092 | 11/1993 | A61L/29/00 |
| WO | WO 95/13704 | 5/1995 | A01N/59/16 |
| WO | WO 96/17595 | 6/1996 | |
| WO | WO 98/41095 | 9/1998 | A01N/59/00 |
| WO | 98/51273 | 11/1998 | |
| WO | WO 00/27390 | 5/2000 | |
| WO | 00/30697 | 6/2000 | |
| WO | 00/44414 | 8/2000 | |
| WO | 00/64505 | 11/2000 | |
| WO | 00/64506 | 11/2000 | |
| WO | WO 00/78281 A1 | 12/2000 | |
| WO | 00/78282 | 12/2000 | |
| WO | 01/15710 | 3/2001 | |
| WO | 01/24839 | 4/2001 | |
| WO | WO 01/26627 | 4/2001 | |
| WO | 01/27365 | 4/2001 | |
| WO | 01/34686 | 5/2001 | |
| WO | 01/41774 | 6/2001 | |
| WO | 01/41819 | 6/2001 | |
| WO | 01/43788 | 6/2001 | |
| WO | 01/49115 | 7/2001 | |
| WO | WO 01/49301 | 7/2001 | |
| WO | 01/49302 | 7/2001 | |
| WO | WO 01/49303 | 7/2001 | |
| WO | 01/70052 | 9/2001 | |
| WO | 01/74300 | 10/2001 | |
| WO | WO 02/09729 A2 | 2/2002 | |
| WO | 02/15698 | 2/2002 | |
| WO | 02/18003 | 3/2002 | |
| WO | 02/18699 | 3/2002 | |
| WO | 02/44625 | 6/2002 | |

OTHER PUBLICATIONS

Thornton, J.A. 1982. Influence of apparatus geometry and deposition conditions on the structure and topography of thick sputtered coatings. J. Vac. Sci. Technol. 11(4): 666–670.

Thornton, J.A. 1982. Coating deposition by sputtering. *Deposition Technologies For Films and Coatings*, Noyes Publications, N.J. pp. 170–237.

Burrell, et al. "Efficacy of Silver–Coated Dressings as Bacterial Barriers in a Rodent Burn Sepsis Model" *Wounds* 1999; 11(4): 64–71.

Demling, et al., "The Role of Silver in Wound Healing: Effects of Silver on Wound Management," *Wounds*, vol. 13, No. 1, Jan./Feb. 2001 Supplement A; pp. 5–14.

Djokic et al., "An Electrochemical Analysis of Thin Silver Films Produced by Reactive Sputtering", *Journal of The Electrochemical Society*, 148 (3) C191–C196 (2001).

Kirsner et al., "The Role of Silver in Wound Healing Part 3: Matrix Metalloproteinsases in Normal and Impaired Wound Healing: A Potential Role of Nanocrystalline Silver", *Wounds* vol. 13, No. 3. May/Jun. 2001, Supplement C, pp. 5–11.

Olson et al., "Healing of Porcine Donor sites Covered with Silver–coated Dressings"* *Eur J Surg* 2000; 166: 486–489.

Ovington, "The Role of Silver in Wound Healing: Why is Nanocrystalline Silver Superior? Nanocrystalline Silver: Where the Old and Familiar Meets a New Frontier," *Wounds*, vol. 13, No. 2, Mar./Apr. 2001, Supplement B; pp. 5–10.

Sant et al., "Novel duplex antimicrobial silver films deposited by magnetron sputtering", *Philosophical Magazine Letters*, 2000, vol. 80, No. 4, 249–256.

Tredget, "Evaluation of Wound Healing using Silver Dressing," Feb. 22, 1996.

Tredget et al., "A Matched Pair, Randomized Study Evaluating the Efficacy and Safety of Acticoat* Silver–Coated Dressing for the Treatment of Burn Wounds," *Journal of Burn Care & Rehabilitation* Nov./Dec. 1998; 19:531–7.

Voigt, et al., "The Use of Acticoat as Silver Impregnated Telfa Dressings in a Regional Burn and Wound Care Center: The Clinicians View," *Wounds*, vol. 13, No. 2, Mar./Apr. 2001, Supplement B; pp. 11–20.

Wright et al., "Early healing events in a porcine model of contaminated wounds: effects of nanocrystalline silver on matrix metalloproteinases, cell apoptosis, and healing" *Wound Repair and Regeneration* 2002; 10:141–151.

Wright, et al., "The Comparative Efficacy of Two Antimicrobial Barrier Dressings: In–vitro Examination of Two Controlled Release of Silver Dressings" *Wounds* vol. 10, No. 6 Nov./Dec. 1998, pp. 179–188.

Wright, et al., "Efficacy of topical silver against fungal burn wound pathogens", *AJIC* vol. 27, No. 4, Aug. 1999.

Wright, et al., "Wound Management in an era of increasing bacterial antibiotic resistance: A role for topical silver treatment," *AJIC* vol. 26, No. 6; pp. 572–577 Dec. 1998.

Yin et al., "Comparative Evaluation of the Antimicrobial Activity of ACTICOAT* Antimicrobial Barrier Dressing" *Journal of Burn Care & Rehabilitation*, vol. 20, No. 3 May/Jun. 1999.

Yin, et al., "Effect of Acticoat Antimicrobial Barrier Dressing on Wound Healing and Graft Take", *Burn Care & Rehabilitation*, part 2, Jan/Feb 1999.

* cited by examiner-

ANTIMICROBIAL BIOABSORBABLE MATERIALS

CROSS-REFERENCE TO RELATED APPLICATIONS

This application takes priority from U.S. Provisional Application Serial No. 60/197,959, filed Apr. 16, 2001, which is incorporated by reference in its entirety herein.

FIELD OF THE INVENTION

The invention relates to bioabsorbable materials, which are rendered antimicrobial due to the presence of antimicrobial metals in the form of coatings or powders; processes for their production; and use of same for controlling infection.

BACKGROUND OF THE INVENTION

The risk of acquiring infections from bioabsorbable materials in medical devices is very high. Many medical applications exist for bioabsorbable materials including:

1) Wound Closures: including for example sutures, staples, adhesives;

2) Tissue Repair: including for example meshes for hernia repair;

3) Prosthetic Devices: including for example internal bone fixation, physical barrier for guided bone regeneration;

4) Tissue Engineering: including for example blood vessels, skin, bone, cartilage, and liver; and 5) Controlled Drug Delivery Systems: including for example microcapsules and ion-exchange resins.

The use of bioabsorbable materials in medical applications such as the above have the advantages of reducing tissue or cellular irritation and induction of inflammatory response from prominent retained hardware; eliminating or decreasing the necessity of hardware removal; and in the case of orthopedic implants, permitting a gradual stress transfer to the healing bone and thus allowing more complete remodeling of the bone.

Bioabsorbable materials for medical applications are well known; for example, U.S. Pat. No. 5,423,859 to Koyfman et al., lists exemplary bioabsorbable or biodegradable resins from which bioabsorbable materials for medical devices may be made. In general, bioabsorbable materials extend to synthetic bioabsorbable, naturally derived polymers, or combinations thereof, with examples as below:

1) Synthetic Bioabsorbable Polymers: for example polyesters/polylactones such as polymers of polyglycolic acid, glycolide, lactic acid, lactide, dioxanone, trimethylene carbonate etc., polyanhydrides, polyesteramides, polyortheoesters, polyphosphazenes, and copolymers of these and related polymers or monomers; and 2) Naturally Derived Polymers:
  a) Proteins: albumin, fibrin, collagen, elastin;
  b) Polysaccharides: chitosan, alginates, hyaluronic acid; and 3) Biosynthetic Polyesters: 3-hydroxybutyrate polymers.

Like other biomaterials, bioabsorbable materials are also subjected to bacterial contamination and can be a source of infections which are difficult to control. Those infections quite often lead to the failure of the devices, requiring their removal and costly antimicrobial treatments.

Prior art efforts to render bioabsorbable materials more infection resistant generally have focused on impregnating the materials with antibiotics or salts such as silver salts. However, such efforts usually provide only limited, and instantaneous antimicrobial activity, which is limited by the availability or solubility of the antimicrobial agent over time. It is desirable to have an antimicrobial effect which is sustained over time, such that the antimicrobial effect can be prolonged for the time that the bioabsorbable material is in place. This can range from hours or days, to weeks or even years.

There are suggestions in the prior at to provide metal coatings, such as silver coatings, on medical devices; for example, International Publication No. WO 92/13491 to Vidal and Redmond; Japanese Patent Application Disclosure No. 21912/85 to Mitsubishi Rayon K. K., Tokyo; and U.S. Pat. No. 4,167,045 to Sawyer. None of these references include teachings specific to the use of metal coatings on bioabsorbable materials. In such applications, it is important that the metal coatings do not shed or leave behind large metal particulates in the body, which will induce unwanted immune responses and/or toxic effects.

There is a need for antimicrobial coatings for bioabsorbable materials, which can create an effective and sustainable antimicrobial effect, which do not interfere with the bioabsorption of the bioabsorbable material, and which do not shed or leave behind large metal particulates in the body as the bioabsorbable material disappears.

SUMMARY OF THE INVENTION

This invention provides bioabsorbable materials comprising a bioabsorbable substrate associated with one or more antimicrobial metals being in a crystalline form characterized by sufficient atomic disorder, such that the bioabsorbable material in contact with an alcohol or water based electrolyte, releases atoms, ion, molecules, or clusters of at least one antimicrobial metal at a concentration sufficient to provide an antimicrobial effect. The one or more antimicrobial metals do not interfere with the bioabsorption of the bioabsorbable material, and do not leave behind particulates larger than 2 $\mu$m, as measured 24 hours after the bioabsorbable material has disappeared. Most preferably, the particulate sizing from the coating or powder is sub-micron, that is less than about 1 $\mu$m, as measured 24 hours after the bioabsorbable material has disappeared. Particulates are thus sized to avoid deleterious immune responses or toxic effects. Such antimicrobial metals are in the form of a continuous or discontinuous coating, a powder, or a coating on a bioabsorbable powder.

The antimicrobial coating is thin, preferably less than 900 nm or more preferably less than 500 nm, and very fine grained, with a grain size (crystallite size) of preferably less than 100 nm, more preferably less than 40 nm, and most preferably less than 20 nm. The antimicrobial coating is formed of an antimicrobial metal, which is overall crystalline, but which is created with atomic disorder, and preferably also having either or both of a) a high oxygen content, as evidenced by a rest potential greater than about 225 mV, more preferably greater than about 250 mV, in 0.15 M $Na_2CO_3$ against a SCE (standard calomel electrode), or b) discontinuity in the coating.

The antimicrobial metal associated with the bioabsorbable substrate may also be in the form of a powder, having a particle size of less than 100 $\mu$m or preferably less than 40 $\mu$m, and with a grain size (crystallite size) of preferably less than 100 nm, more preferably less than 40 nm, and most preferably less than 20 nm. Such powders may be prepared as a coating preferably of the above thickness, onto powdered biocompatible and bioabsorbable substrates; as a nanocrystalline coating and converted into a powder; or as a powder of the antimicrobial metal which is cold worked to impart atomic disorder.

A method of preparing the above antimicrobial bioabsorbable materials is also provided, with the bioabsorbable substrate being formed from a bioabsorbable polymer, or being a medical device or part of a medical device. The coating or powder of the one of more antimicrobial metals is formed by either physical vapour deposition under specified conditions and/or by forming the antimicrobial material as a composite material; or by cold working the antimicrobial material containing the antimicrobial metal at conditions which retain the atomic disorder, as in the case where the antimicrobial metal is in the form of a powder. Sufficient oxygen is incorporated in the coating or powder such that particulates of the antimicrobial metals during dissociation are sized at preferably less than 2 μm, or preferably less than 1 μm, to avoid deleterious immune responses or toxic effects, As used herein, the terms and phrases set out below have the meanings which follow.

"Alcohol or water-based electrolyte" is meant to include any alcohol or water-based electrolyte that the anti-microbial coatings of the present invention might contact in order to activate (i.e. cause the release of species of the anti-microbial metal) into same. The term is meant to include alcohols, saline, water, gels, fluids, solvents, and tissues containing water, including body fluids (for example blood, urine or saliva), and body tissue (for example skin, muscle or bone).

"Antimicrobial effect" means that atoms, ions, molecules or clusters of the anti-microbial metal (hereinafter "species" of the anti-microbial metal) are released into the alcohol or electrolyte which the material contacts in concentrations sufficient to inhibit bacterial (or other microbial) growth in the vicinity of the material. The most common method of measuring anti-microbial effect is by measuring the zone of inhibition (ZOI) created when the material is placed on a bacterial lawn. A relatively small or no ZOI (ex. less than 1 mm) indicates a non useful anti-microbial effect, while a larger ZOI (ex. greater than 5 mm) indicates a highly useful anti-microbial effect. One procedure for a ZOI test is set out in the Examples which follow.

"Antimicrobial metals" are metals whose ions have an anti-microbial effect and which are biocompatible. Preferred anti-microbial metals include Ag, Au, Pt, Pd, Ir (i.e., the noble metals), Sn, Cu, Sb, Bi and Zn, with Ag being most preferred.

"Atomic disorder" includes high concentrations of: point defects in a crystal lattice, vacancies, line defects such as dislocations, interstitial atoms, amorphous regions, gain and sub grain boundaries and the like relative to its normal ordered crystalline state. Atomic disorder leads to irregularities in surface topography and inhomogeneities in the structure on a nanometer scale.

"Bioabsorbable materials" are those useful in medical devices or parts of medical devices, that is which are biocompatible, and which are capable of bioabsorption in a period of time ranging from hours to years, depending on the particular application.

"Bioabsorption" means the disappearance of materials from their initial application site in the body (human or mammalian) with or without degradation of the dispersed polymer molecules.

"Biocompatible" means generating no significant undesirable host response for the intended utility.

"Cold working" as used herein indicates that the material has been mechanically worked such as by milling, grinding, hammering, mortar and pestle or compressing, at temperatures lower than the recrystallization temperature of the material. This ensures that atomic disorder imparted through working is retained in the material.

"Diffusion", when used to describe conditions which limit diffusion in processes to create and retain atomic disorder, i.e. which freeze-in atomic disorder, means diffusion of atoms and/or molecules on the surface or in the matrix of the material being formed.

"Dissociation" means the breakdown of the antimicrobial metal in the form of a coating or powder associated with the bioabsorbable substrate, when the bioabsorbable material is in contact with an alcohol or water based electrolyte.

"Grain size", or "crystallite size" means the size of the largest dimension of the crystals in the anti-microbial metal coating or powder.

"Metal" or "metals" includes one or more metals whether in the form of substantially pure metals alloys or compounds such as oxides, nitrides, borides, sulphides, halides or hydrides.

"Nanocrystalline" is used herein to denote single-phase or multi-phase polycrystals, the grain size of which is less than about 100, more preferably <50 and most preferably <25 nanometers in at least one dimension. The term, as applied to the crystallite or grain size in the crystal lattice of coatings, powders or flakes of the anti-microbial metals, is not meant to restrict the particle size of the materials when used in a powder form.

"Normal ordered crystalline state" means the crystallinity normally found in bulk metal materials, alloys or compounds formed as cast, wrought or plated metal products. Such materials contain only low concentrations of such atomic defects as vacancies, grain boundaries and dislocations.

"Particulate size" means the size of the largest dimension of the particulates which are shed or left behind in the body from the antimicrobial coatings on the bioabsorbable materials.

"Powder" is used herein to include particulate sizes of the nanocrystalline anti-microbial metals ranging from nanocrystalline powders to flakes "Sustained release" or "sustainable basis" are used to define release of atoms, molecules, ions or clusters of an anti-microbial metal that continues over time measured in hours or days, and thus distinguishes release of such metal species from the bulk metal, which release such species at a rate and concentration which is too low to achieve an anti-microbial effect and from highly soluble salts of anti-microbial metals such as silver nitrate, which releases silver ions virtually instantly, but not continuously, in contact with an alcohol or electrolyte.

DESCRIPTION OF THE PREFERRED EMBODIMENTS

A. Bioabsorbable Materials

Bioabsorbable materials for medical applications are well known, and include bioabsorbable polymers made from a variety of bioabsorbable resins; for example, U.S. Pat. No. 5,423,859 to Koyfman et al., lists exemplary bioabsorbable or biodegradable resins from which bioabsorbable materials for medical devices may be made. Bioabsorbable materials extend to synthetic bioabsorbable or naturally derived polymers, with typical examples as below:

1) Synthetic Bioabsorbable Polymers: for example polyesters/polylactones such as polymers of polyglycolic acid, glycolide, lactic acid, lactide, dioxanone, trimethylene carbonate etc., polyanhydrides, polyesteramides, polyortheoesters, polyphosphazenes, and copolymers of these and related polymers or monomers, 2) Naturally Derived Polymers:
   a) Proteins: albumin, fibrin, collagen, elastin;
   b) Polysaccharides: chitosan, alginates, hyaluronic acid; and
3) Biosynthetic Polyesters: 3-hydroxybutyrate polymers The bioabsorbable material, depending on the application, may be used in a powder, sheet or fibre form.

Many medical applications exist for bioabsorbable materials coated with the antimicrobial coatings of this invention, including, without limitation:

1) Wound closures: including for example sutures, staples, and adhesives,
2) Tissue Repair: including for example meshes for hernia repair;
3) Prosthetic Devices: including for example internal bone fixation, physical barrier for guided bone regeneration;
4) Tissue Engineering: including for example blood vessels, skin, bone, cartilage, and liver;
5) Controlled Drug Delivery Systems: including for example microcapsules and ion-exchange resins; and
6) Wound Coverings or Fillers: including for example alginate dressings and chitosan powders.

B. Antimicrobial Coating for Bioabsorbable Materials

The bioabsorbable material includes an antimicrobial coating formed from an antimicrobial metal, which is formed by the procedure set out below. The coating can be applied as one or more of the layers, but is most preferably applied as a discontinuous coating of a single thin layer which is less than 900 nm in thickness, more preferably less than 500 nm, and which has a grain size (i.e. crystallite size in the coating itself) less than 100 nm, more preferably less than 40 nm, and most preferably less than 20 nm.

The coating is most preferably formed with atomic disorder in accordance with the procedures set out above and as described in International Publication Nos. WO 98/41095, WO 95/13704, and WO 93/23092, all to Burrell et al. In addition, the coating is preferably formed with a high oxygen content, as determined by a positive rest potential greater than 225 mV, more preferably greater than about 250 mV, in 0.15 M $Na_2CO_3$ against a SCE, when measured in accordance with the procedure set out in Example 5. The high oxygen content is achieved by including oxygen in the working gas atmosphere during the physical vapour deposition technique. Preferably the ratio of inert working gas (preferably argon) to oxygen is about 96:4 or less.

The antimicrobial coating can be rendered discontinuous by many techniques, for instance by coating fibers or powders from only one side, with or without rotation or vibration, by making the coatings so thin as to be discontinuous, by coating on porous fibrous materials so as to achieve discontinuity, by masking either the substrate or the cathode, or to etch a continuous coating.

The above features of the antimicrobial coatings of this invention have been found to ensure that the particulate size left behind by the antimicrobial coatings as the bioabsorbable material disappears, are less than about 2 μm in size, and more preferably are less than 1 μm in size.

The antimicrobial coating is formed in a crystalline form from antimicrobial metals with atomic disorder so as to produce an antimicrobial effect. The production of atomic disorder through physical vapour deposition techniques is described in the above mentioned PCT applications to Burrell et al. and as outlined below.

The antimicrobial metal is deposited as a thin metallic film on one or more surfaces of the bioabsorbable material by vapour deposition techniques. Physical vapour techniques, which are well known in the art, all deposit the metal from the vapour, generally atom by atom, onto a substrate surface. The techniques include vacuum or arc evaporation, sputtering, magnetron sputtering and ion plying. The deposition is conducted in a manner to create atomic disorder in the coating as defined above. Various conditions responsible for producing atomic disorder are useful. These conditions are generally those which one has been taught to avoid in thin film deposition techniques, since the object of most thin film depositions is to create a defect free, smooth and dense film (see for example J. A. Thornton, J. Vac. Sci. Technol., Vol 11, (4); 666–670; and "Coating Deposition by Sputtering" in Deposition Technologies For Films and Coatings, Noyes Publications, N.J. 170–237, (1982)). The preferred conditions which are used to create atomic disorder during the deposition process include:

a low substrate temperature, that is maintaining the surface to be coated at a temperature such that the ratio of the substrate temperature to the melting point of the metal (in degrees Kelvin) is less than about 0.5, more preferably less than about 0.35 and most preferably less than about 0.3; and optionally one or both of:

a higher than normal working (or ambient) gas pressure, i.e. for vacuum evaporation: e-beam or are evaporation, greater than 0.01 mT, gas scattering evaporation (pressure plating) or reactive are evaporation, greater than 20 mT; for sputtering: greater than 75 mT; for magnetron sputtering: greater than about 10 mT; and for ion plating: greater than about 200 mT; and maintaining the angle of incidence of the coating flux on the surface to be coated at less than about 75°, and preferably less than about 30°.

The metals used in the coating are those known to release ions etc. having an antimicrobial effect, as set out above. For bioabsorbable materials, the metal must also be biocompatible. Preferred metals include the noble metals Ag, Au, Pt, Pd, and Ir as well as Sn, Cu, Sb, Bi, and Zn or alloys or compounds of these metals or other metals. Most preferred is Ag or Au, or alloys or compounds of one or more of these metals. Particularly preferred is Ag.

For economic reasons, the thin metal film has a thickness no greater than that needed to provide release of metal ions on a sustainable basis over a suitable period of time. Within the preferred ranges of thicknesses set out above, the thickness will vary with the particular metal in the coating (which varies the solubility and abrasion resistance), and with the degree of atomic disorder in (and thus the solubility of) the coating. The thickness will be thin enough that the coating does not interfere with the dimensional tolerances or flexibility of the device for its intended utility.

The antimicrobial effect of the material so produced is achieved when the coating is brought into contact with an alcohol or a water-based electrolyte, thus releasing metal ions, atoms, molecules or clusters. The concentration of the metal species which is needed to produce an antimicrobial effect will vary from metal to metal. Generally, an antimicrobial effect is achieved with silver coatings in body fluids such as plasma, serum or urine at concentrations less than about 0.5–10 μg/ml of silver species. Evidence of the antimicrobial effect of the material may be demonstrated by biological testing. Localized antimicrobial effect is demonstrated by zone of inhibition testing (see Example 1), whereas sustained release of the antimicrobial metal is illustrated by log reduction (see Examples 2 and 4).

The ability to achieve release of metal atoms, ions, molecules or clusters on a sustainable basis from a coating is dictated by a number of factors, including coating characteristics such as composition, structure, solubility and thickness, and the nature of the environment in which the device is used. As the level of atomic disorder is increased, the amount of metal species released per unit time increases. For instance, a silver metal film deposited by magnetron sputtering at T/Tm<0.5 and a working gas pressure of about 7 mTorr releases approximately ⅓ of the silver ions that a film deposited under similar conditions, but at 30 mTorr, will release over 10 days. Films that are created with an intermediate structure (ex. lower pressure, lower angle of incidence etc.) have Ag release values intermediate to these values as determined by bioassays. This then provides a method for producing controlled release metallic coatings. Slow release coatings are prepared such that the degree of disorder is low while fast release coatings are prepared such that the degree of disorder is high.

The time required for total dissolution will be a function of the film thickness, the composition of the film and the nature of the environment to which the film is exposed. The relationship in respect of thickness is approximately linear, i.e., a two-fold increase in film thickness will result in about a two-fold increase in longevity.

It is also possible to control the metal release from a coating by forming a thin film coating with a modulated structure. For instance, a coating deposited by magnetron sputtering such that the working gas pressure was low (ex. 15 mTorr) for 50% of the deposition time and high (ex. 30 mTorr) for the remaining time, has a rapid initial release of metal ions, followed by a longer period of slow release. This type of coating is extremely effective on devices such as urinary catheters for which an initial rapid release is required to achieve immediate antimicrobial concentrations followe by a lower release rate to sustain the concentration of metal ions over a period of weeks.

The substrate temperature used during vapour deposition should not be so low that annealing or recrystallization of the coating takes place as the coating warms to ambient temperatures or the temperatures at which it is to be used (ex. body temperature). This allowable ΔT, that the temperature differential between the substrate temperature during deposition and the ultimate temperature of use, will vary from metal to metal. For the most preferred metals of Ag and Au, preferred substrate temperatures of −20° C. to 200° C., more preferably −10° C. to 100° C. are used.

Atomic disorder may also be achieved by preparing composite metal materials, that is materials which contain one or more antimicrobial metals in a metal matrix which includes atoms or molecules different from the antimicrobial metals, such that the inclusion of the different materials creates atomic disorder in the crystalline lattice.

The preferred technique for preparing a composite material is to co- or sequentially deposit the antimicrobial metal (s) with one or more other inert, biocompatible metals selected from Ta, Ti, Nb, Zn, V, Hf, Mo, Si, Al and alloys of these metals or other metal elements, typically other transition metals. Such inert metals have a different atomic radii from that of the antimicrobial metals, which results in atomic disorder during deposition. Alloys of this kind can also serve to reduce atomic diffusion and thus stabilize the disordered structure. Thin film deposition equipment with multiple targets for the placement of each of the antimicrobial and inert metals is preferably utilized. When layers are sequentially deposited the layer(s) of the inert metal(s) should be discontinuous, for example as islands within the antimicrobial metal matrix. The final ratio of the antimicrobial metal(s) to inert metal(s) should be greater than about 0.2. The most preferable inert metals are Ti, Ta, Zn and Nb. It is also possible to form the antimicrobial coating from oxides, carbides, nitrides, sulphides, borides, halides or hydrides of one or more of the antimicrobial metals and/or one or more of the inert metals to achieve the desired atomic disorder.

Another composite material may be formed by reactively co- or sequentially depositing, by physical vapour techniques, a reacted material into the thin film of the antimicrobial metal(s). The reacted material is an oxide, nitride, carbide, boride, sulphide, hydride or halide of the antimicrobial and/or inert metal, formed in situ by injecting the appropriate reactants, or gases containing same, (ex. air, oxygen, water, nitrogen, hydrogen, boron, sulphur, halogens) into the deposition chamber. Atoms or molecules of these gases may also become absorbed or trapped in the metal film to create atomic disorder. The reactant may be continuously supplied during deposition for codeposition or it may be pulsed to provide for sequential deposition. The final ratio of antimicrobial metal(s) to reaction product should be greater than about 0.2. Air, oxygen, nitrogen and hydrogen are particularly preferred reactants.

The above deposition techniques to prepare composite coatings may be used with or without the conditions of lower substrate temperatures, high working gas pressures and low angles of incidence set out above. One or more of these conditions are preferred to retain and enhance the amount of atomic disorder created in the coating.

C. Antimicrobial Powder for Bioabsorbable Materials

Antimicrobial powders for bioabsorbable materials are preferably nanocrystalline powders formed with atomic disorder. The powders either as pure metals, metal alloys or compounds such as metal oxides or metal salts, can be formed by vapour deposition, mechanical working, or compressing to impart atomic disorder, as set out below. Mechanically imparted disorder is conducted under conditions of low temperature (i.e. temperatures less than the temperature of recrystallization of the material) to ensure that annealing or recrystallization does not take place.

Nanocrystalline powders may comprise powders of the antimicrobial metal itself, or bioabsorbable powders which are coated with the antimicrobial metal, as demonstrated in Example 4 in which a chitosan powder is coated with silver.

Nanocrystalline powders of the antimicrobial metals may be prepared by several procedures as set out above, and as described in international Publication Nos. WO 93/23092 and WO 95/13704, both to Burrell et al.; or as otherwise known in the art. In general, nanocrystalline powders may be prepared as a nanocrystalline coating (formed with atomic disorder in accordance with procedures previously described) preferably of the above thickness, onto powdered biocompatible and bioabsorbable substrates such as chitin; or may be prepared as a nanocrystalline coating onto a substrate such as a cold finger or a silicon wafer, with the coating then scraped off to form a nanocrystalline powder.

Alternatively, fine grained or nanocrystalline powders of the anti-microbial metals may be cold worked to impart atomic disorder, whereby the material has been mechanically worked such as by milling, grinding, hammering, mortar and pestle or compressing, at temperatures lower than the recrystallization temperature of the material to ensure that atomic disorder is retained in the material (International Publication Nos. WO 93/23092 and WO 95/13704, both to Burrell et al.,). Nanocrystalline powders may be sterilized with gamma radiation as described below to maintain atomic disorder, hence the antimicrobial effect.

The prepared nanocrystalline powders may then be incorporated into or onto the bioabsorbable substrate by any methods known in the art. For example, the nanocrystalline powders may be layered onto the bioabsorbable substrate as a coating; mechanically mixed within the fibers of the bioabsorbable substrate; or impregnated into the bioabsorbable substrate by physical blowing. The quantity of nanocrytalline powder impregnating a bioabsorbable substrate could be adjusted accordingly to achieve a desired dose range. Alternatively, the nanocrystalline powder may be incorporated into a polymeric, ceramic, metallic matrix, or other matrices to be used as a material for the manufacture of bioabsorbable substrates, medical devices or parts of medical devices, or coatings therefor.

The antimicrobial effect of the nanocrystalline powders is achieved when the substrate, coated or impregnated with the nanocrystalline powder, is brought into contact with an alcohol or a water-based electrolyte, thus releasing the antimicrobial metal ions, atoms, molecules or clusters.

D. Sterilization

Bioabsorbable materials once coated with the antimicrobial coating or powder of an antimicrobial metal formed with atomic disorder are preferably sterilized without applying excessive thermal energy, which can anneal out the atomic disorder, thereby reducing or eliminating a useful antimicrobial effect. Gamma radiation is preferred for sterilizing such dressings, as discussed in International Publication No. WO 95/13704 to Burrell et al.

The sterilized materials should be sealed in packaging which excludes light penetration to avoid additional oxidation of the antimicrobial coating. Polyester peelable pouches are preferred. The shelf life of bioabsorbable, antimicrobial materials thus sealed should be over one year.

E. Use of Bioabsorbable Materials With Antimicrobial Coating or Powder

The antimicrobial coatings and powders of this invention are activated by contacting an alcohol or water-based electrolyte. If the bioabsorbable material is to be used in an application which does not provide exposure to an electrolyte, the material can be moistened with drops of sterile water or 70% ethanol, in order to activate the coating for release of antimicrobial metal species. In a dressing form, the bioabsorbable material can be secured in place with an occlusive or semi-occlusive layer, such as an adhesive film, which will keep the dressing in a moist environment.

F. EXAMPLES

Example 1

Silver-Coated Bioabsorbable Sutures 1.1 Bioabsorbable Material

Nanocrystalline silver coating was prepared on a bioabsorbable suture. The bioabsorbable material coated was DEXON™ II BI-COLOR (Braided polyglycolic acid with polycaprolate coating) manufactured by Sherwood Medical Corp. (St. Louis, Mo., USA).

1.2 Sputtering Conditions

The coating layer on only one side of the bioabsorbable suture was formed by magnetron sputtering under the following conditions:

| Target: | 99.99% Ag |
|---|---|
| Target Size; | 20.3 cm diameter |
| Working Gas: | 96/4 wt % Ar/O$_2$ |
| Workitig Gas Pressure: | 40 mTorr |
| Power: | 0.11 kW |
| Substrate Temperature: | 20° C. |
| Base Pressure: | 4.0 × 10$^{-6}$ Tort |
| Anode/Cathode Distance: | 100 mm |
| Sputtering Time/Film Thickness: | 16 min/500 nm |
| Voltage: | 360 V |

With these sputtering conditions applied to the suture material on only one side, a discontinuous coating which only covers two thirds of the suture surface was achieved. This coating method gave an open circuit potential greater than 225 mV (in Na$_2$CO$_3$, against SCE, as in Example 5) and a crystallite size less than 20 nm as confirmed by x-ray diffraction (XRD) test.

1.3 Zone of Inhibition Test

To establish that silver species were released from the coated bioabsorbable suture and to demonstrate antimicrobial effect, a zone of inhibition test was conducted. Mueller Hinton agar was dispensed into Petri dishes. The agar plates were allowed to dry the surfaces prior to being inoculated with lawns of *Pseudomonas aeruginosa* ATCC 27317 and *Staphylococcus aureus* ATCC 25923. Immediately after inoculation, the coated suture segments (one inch long) were placed on the center of the plate. The Petri dishes were incubated at 37° C. for 24 hours, and the zone of inhibition (ZOI) was measured therafter. The results showed that the average ZOIs (triplicate samples) were 9.0 mm and 7.6 mm against *Pseudomonas aeruginosa* and *Staphylococcus aureus* respectively. These inhibition zones were remarkable considering the very small diameter (0.38 mm) of the suture.

1.4 Tensile Strength Test

To demonstrate that the silver coating did not inhibit the bioabsorption of the suture, the following tensile strength test was conducted. The suture was cut into segments of 10 inch lengths, and coated with silver using the sputtering conditions mentioned above. The coated and uncoated sutures were placed in beakers containing 50% fetal bovine serum (Gibco/BRL, Life Technologies Corp., Ontario, Canada) in phosphate buffered saline (PBS, pH 7.2). The beakers were incubated at 37° C. Samples were taken out for tensile strength test using Instron Series IX Automated Material Testing System 1.04 (sample rate: 10.00 pts/sec, crosshead speed: 0.500 in/min, humidity: 50%, temperature: 73° F.) at days 1, 2 and 4. The percentage of tensile remaining (% breaking tensile of treated suture/breaking tensile of untreated suture×100%) was calculated. The results are shown in the Table 1.

TABLE 1

| Tensile remaining (%) of PBS-Calf serum treated sutures | | | |
|---|---|---|---|
| Sample | Day 1 | Day 2 | Day 4 |
| Uncoated suture | 98.7 | 96.4 | 91.8 |
| Silver-coated suture | 96.8 | 93.5 | 88.2 |

It will be noted from Table 1, that the silver coatings did not impede the bioabsorption of the suture material, in that the tensile remaining was similar for both uncoated and silver-coated suture.

Example 2

Silver Coated Bioabsorbable Alginate Wound Dressing 2.1 Bioabsorbable Material

Kaltostat™ calcium-sodium alginate dressing (ConvaTec, Princeton, N.J., USA) was coated with nanocrystalline silver.

2.2 Sputtering Conditions

The coating layer on the bioabsorbable alginate wound dressing was formed by magnetron sputtering under the following conditions:

| | |
|---|---|
| Target: | 99.99% Ag |
| Target Size: | 20.3 cm diameter |
| Working Gas: | 96/4 wt % Ar/O$_2$ |
| Working Gas Pressure: | 40 mTorr |
| Power: | 0.10 kW |
| Substrate Temperature: | 20° C. |
| Base Pressure: | 4.0 × 10$^{-6}$ Torr |
| Anode/Cathode Distance: | 100 mm |
| Sputtering Time/Film Thickness: | 30 min/800 nm |
| Voltage: | 360 V |

Because of the discontinuity of the fibers at the surface of the dressing, this coating represented a discontinuous coating.

2.3 Bacterial Killing Capacity Test

To demonstrate the bactericidal effect of the coated alginate dressing, a bacterial killing capacity test was conducted. The coated alginate dressing was cut into one square inch pieces. *Pseudomonas aeruginosa* ATCC 27317 colonies from an overnight culture were inoculated in 5 ml of Tryptic Soy Broth (TSB) and incubated at 37° C. until the suspension reached 0.5 McFarland turbidity. 0.5 ml of the bacterial suspension were inoculated onto each piece of the dressings and incubated at 37° C. for two hours. The survival bacteria in the dressing were recovered by vortexing the dressing in 4.5 ml of STS (0.85% sodium chloride, 1% Tween™ 20 and 0.4% sodium thioglycollate) solution. The bacteria in the solution were enumerated by plate counting and the log reduction was calculated. The result showed that the tested silver-coated alginate dressing induced 6.2 log reduction in the two hour test period, thus demonstrating an excellent bacterial killing capacity of the silver-coated alginate dressing.

2.4 Evidence of Bioabsorption

Silver-coated Kaltostat dressing and uncoated controls (three pieces of each in one square inch) were weighed before testing. Then the dressings were placed in Petri dishes each containing 30 ml of fetal bovine serum (Gibco/BRL, Life Technologies Corp., Ontario, Canada) and incubated at 37° C. for three days. The dressings were dried in an oven at 60° C. overnight and weighed again. Although degradation could be seen in the dishes, the post-weight was higher than pre-weight because the dressing had absorbed a lot of water and formed a gel. For this reason, a relative weight was calculated. The results showed that the relative weights were 1.69±0.18 and 1.74±0.12 for uncoated control Kaltostat dressing and silver-coated dressing respectively. The difference was not statistically significant.

Example 3

Double Side Coated Alginate Wound Dressing 3.1 Bioabsorbable Material

Needled calcium alginate fabric was purchased from Acordis Specialty Fibers Corp. (Coventry, UK).

3.2 Sputtering Conditions

The dressing was sputtered on both sides using a four-pass process with two passes for each side. The Westaim Biomedical TMRC unit was used to coat the dressing under the following conditions.

| | |
|---|---|
| Target: | 99.99% Ag |
| Target Size; | 15.24 cm × 152.4 cm |

| | |
|---|---|
| Working Gas: | 10/20 wt % Ar/O$_2$ - Base coat |
| | 100/0 wt % Ar/O$_2$ - Top coat |
| Working Gas Pressure: | 40 mTorr |
| Total current: | 81 A For the first and second passes |
| | 17 A for the third and fourth passes |
| Base Pressure: | 5.0 × 10$^{-5}$ Torr |
| Web Speed: | 230 mm/min - Base coat |
| | 673 mm/min - Top coat |
| Voltage: | 430 V - Base coat |
| | 300 V - Top coat |

3.3 Evidence of Biodegradation

Degradation of the double side coated alginate wound dressing in an aqueous solution resulted in an increase of viscosity in that solution. The following test monitored the increase in viscosity as an indicator of biodegradation in vitro. The silver coated alginate dressing and uncoated control alginate dressing were cut into 2"×2" pieces. Four pieces of each dressing (16 square inch in total) were placed in a beaker containing 80 ml of phosphate buffered saline. The beakers were incubated in a shaking incubator at 37±1° C. and 120±5 rpm for 48±2 hours. After vigorously swirling for ten seconds, the solutions were removed for viscosity analysis. The measuring system used was Z1 DIN with a shear rate range from 0 to 2500 l/s.

Thirty data points were collected at 60 second intervals. The results are reported and observed as a chart with a shear rate as the x axis and viscosity as the y axis. Since the viscosity of the solution tends to become stabilized after a shear rate of 1000 l/s, three readings of the viscosity at 1400, 1600 and 1800 l/s are averaged to obtain the viscosity of the solution. Such data showed that silver-coated alginate dressing generated an average viscosity of 3.1 cP while control alginate dressing 3.0 cP. These results suggest that both dressings have a very similar degradation rate, which indicates that the silver coating has no significant impact on the degradation of alginate material.

Example 4

Silver-Coated Chitosan Powder 4.1 Bioabsorbable Material

Chitosan is a partially deacetylated form of chitin, a natural polysaccharide. It can be degraded by lysozyme and absorbed by body. There have been studies shown that it accelerate wound healing in small animals as rats and dogs (Shigemasa Y. et al., Biotechnology and Genetic Engineering Reviews 1995; 13:383–420). The material used for coating was a fine cream-colored chitosan powder purchased from ICN Biomedicals Inc. (Aurora, Ohio, USA).

4.2 Sputtering Conditions

The chitosan powder was coated by magnetron sputtering under the following conditions:

| | |
|---|---|
| Target: | 99.99% Ag |
| Target Size: | 20.3 cm diameter |
| Working Gas: | 80/20 wt % Ar/O$_2$ |
| Working Gas Pressure: | 30 mTorr |
| Power: | 0.2 kW |
| Substrate Temperature: | 20° C. |
| Base Pressure: | 6.0 × 10$^{-6}$ Torr |
| Anode/Cathode Distance: | 100 mm |
| Sputtering Time/Film Thickness: | 10 min |
| Voltage: | 409 V |

As in Example 1, these coating conditions resulted in a discontinuous coating of silver, estimated at 400–500 nm thick, being applies from one side only.

4.3 Bacterial Killing Capacity Test

The test was similar to that used for the Alginate dressing in Example 2 to demonstrate bactericidal ability of the material. The silver-coated chitosan powder samples (0.03 g) were mixed with 0.3 ml of Pseudomonas aeruginosa grown in TSB ($10^7$ cells/ml) and incubated at 37° C. for 30 minutes or 2 hours. The silver activity was stopped by addition of 2.7 ml of STS solution. The numbers for bacterial survival were determined using standard plate count techniques. The results showed that the silver-coated chitosan powder reduced the number of viable bacteria to undetectable levels both at 30 minutes and 2 hours.

Example 5

X-ray Diffraction and Rest Potential Measurements

Samples of the antimicrobial coatings of the present invention were prepared on glass substrates in order to measure the crystallite sizes and the rest potential. The sputtering conditions are set out in Table 2 below. The conditions were similar to those set out in Examples 1 and 2 above, but used varying oxygen content in the working gas, as given in Table 2. A comparison coating of pure silver (i.e., sputtered in 100% Ar) was also prepared. The sputtered films were then analyzed by x-ray diffraction to determine the crystallite size, measured for silver along the Ag(111) line, and to estimate for silver oxide by measuring along the $Ag_2O(111)$. The films were also examined electrochemically to determine the rest potential or open circuit potential (OCP). The latter measurement was conducted to confirm a high oxygen content in the films. The rest potential was obtained by two procedures, one being a measurement for 15 minutes in 0.15 M KOH solution and the second being a measurement for 20 minutes in 0.15 M $Na_2CO_3$ solution, both being against a saturated calomel electrode (SCE). The results are set out in Table 3.

REFERENCES

Shigemasa Y. and Minami, S. 1995. Applications of chitin and chitosan for biomaterials. Biotechnology and Genetic Engineering Reviews 13: 383–420.

Thornton, J. A. 1982. Influence of apparatus geometry and deposition conditions on the structure and topography of thick sputtered coatings. J. Vac. Sci. Technol. 11(4): 666–670.

Thornton, J. A. 1982. Coating deposition by sputtering. *Deposition Technologies For Films and Coatings*, Noyes Publications, N. J. pp 170–237.

PATENT DOCUMENTS

Burrell, R. E., Apte, P. S., McIntosh, C. L., Sant, S. B., Gill, K. S., Morris, L. R., and Precht, R. J. Anti-microbial materials. International Publication No. WO 95/13704, published May 26, 1995.

Burrell, R. E. and Morris, L. R. Anti-microbial coating for medical devices. International Publication No. WO 93/23092, published Nov. 25, 1993.

Burrell, R. E. and Precht, R. J. Anti-microbial coatings having indicators and wound dressings. International Publication No. WO 98/41095, published Sep. 24, 1998.

Koyman, I and Chesterfield, M. P. Jet entangled suture yarn and method for making same. U.S. Pat. No. 5,423,859, issued Jun. 13, 1995.

Mitsubishi Rayon K. K., Tokyo. Process for the preparation of metal deposition carrying synthetic fibre staples. Japanese Patent Application Disclosure No. 21912/85, published Feb. 4, 1985.

Sawyer, P. N. Cardiac and vascular prostheses. U.S. Pat. No. 4,167,045, issued Sep. 11, 1979.

Vidal, C. and Redmond, R. J. Improved surgical hardware with bacteriostatic silver coating, and method of using same. International Publication No. WO 92/13491, published Aug. 20, 1992.

All publications mentioned in this specification are indicative of the level of skill in the art to which this invention pertains. All publications are herein incorporated by reference to the same extent as if each individual publication was specifically and individually indicated to be incorporated by reference.

Although the foregoing invention has been described in some detail by way of illustration and example, for purposes of clarity and understanding it will be understood that certain changes and modifications may be made without departing from the scope or spirit of the invention as defined by the following claims.

TABLE 2

Sputtering Conditions for Samples

| Sample number | Sample Ratio Ar:$O_2$ | Base P mTorr | Gas P mTorr | Current [A] | Voltage [V] | Power [kW] | Dep. Time [min.] | Thick. [nm] |
|---|---|---|---|---|---|---|---|---|
| 1 | 100:0 | 2.3 × $10^{-6}$ | 40 ± 0.5 | 0.81 | 345 | 0.252 | 10 | 749 |
| 2 | 96:4 | 2.7 × $10^{-6}$ | 40 ± 0.4 | 0.81 | 400 | 0.290 | 10 | 944 |
| 3 | 94:6 | 2.5 × $10^{-6}$ | 40 ± 0.3 | 0.81 | 410 | 0.300 | 10 | 1120 |
| 4 | 92:8 | 1.7 × $10^{-6}$ | 40 ± 0.5 | 0.811 | 424 | 0.309 | 10 | 1130 |
| 5 | 96:4 | 3.0 × $10^{-6}$ | 40 ± 0.4 | 0.320 | 364 | 0.107 | 30 | 1010 |

TABLE 3

Rest Potentials for Samples under Sputtering Conditions of Table 2

| Sample number | Sample Ratio Ar:$O_2$ | Crystallite Size [nm] | OCP [mV] 0.15 M $Na_2CO_3$ | OCP [mV] 0.15 M KOH |
|---|---|---|---|---|
| 1 | 100:0 | 123.9 | 148 | −13 |
| 2 | 96:4 | 15.4 | 269 | 141 |
| 3 | 94:6 | 10.5 | 265 | 138 |
| 4 | 92:8 | 8.2 | 259 | 133 |
| 5 | 96:4 | est. as 13–20 | >+720 | >+650 |

We claim:

1. A bioabsorbable material comprising:
   a bioabsorbable substrate having a surface; and
   one or more antimicrobial metals associated with the bioabsorbable substrate, the one or more antimicrobial metals being in a crystalline form characterized by sufficient atomic disorder, such that the material in contact with an alcohol or water-based electrolyte, releases atoms, ions, molecules, or clusters of at least one antimicrobial metal at a concentration sufficient to provide a localized antimicrobial effect, and wherein the one or more antimicrobial metals are associated with the bioabsorbable substrate such that particulates of the one or more antimicrobial metals formed during dissociation are sized to avoid deleterious immune responses or toxic effects,
   wherein the bioabsorbable substrate is in the form of a a microcapsule, a dressing, an implant, a wound closure, a suture, a staple, an adhesive, a mesh, a prosthetic device, a controlled drug delivery system, a wound covering or a filler.

2. The material of claim 1, wherein the one or more antimicrobial metals associated with the bioabsorbable substrate are in the form of a continuous or discontinuous coating or a powder.

3. The material of claim 1, wherein the one or more antimicrobial metals associated with the bioabsorbable substrate are in the form of a coating on a powder.

4. The material of claim 2, wherein the one or more antimicrobial metals are formed as discontinuous coatings and/or with sufficient high oxygen content that the particulate of the one or more antimicrobial metals formed during dissociation has a size of less than 2 μm.

5. The material of claim 4, wherein the particulate has a size of less than 1 μm.

6. The material of claim 2, wherein the one or more antimicrobial metals are provided in the form of a coating, having a thickness of less than 900 nm.

7. The material of claim 6, wherein the one or more antimicrobial metals are provided in the form of a coating, having a thickness of less than 500 nm.

8. The material of claim 2, wherein the one or more antimicrobial metals are provided in the form of a powder, having a particle size of less than 100 μm.

9. The material of claim 8, wherein the one or more antimicrobial metals are provided in the form of a powder, having a particle size of less than 40 μm.

10. The material of claim 2, wherein the one or more antimicrobial metals are in the form of a nanocrystalline coating or powder, formed with sufficient atomic disorder to provide sustained release of atoms, ions, molecules, or clusters of the one or more antimicrobial metals.

11. The material of claim 10, wherein the nanocrystalline coating or powder has a crystallite size of less than 100 nm.

12. The material of claim 10, wherein the nanocrystalline coating or powder has a grain size less than 40 nm.

13. The material of claim 10, wherein the nanocrystalline coating or powder has a grain size less than 20 nm.

14. The material of claim 13, wherein the one or more antimicrobial metals are selected from the group consisting of Ag, Au, Pt, Pd, Ir, Sn, Cu, Sb, Bi, Zn, or alloys or compounds thereof.

15. The material of claim 11, wherein at least one of the one or more antimicrobial metals is Ag or Au, or alloys or compounds thereof.

16. The material of claim 11, wherein the antimicrobial metal is silver, or an alloy or compound thereof.

17. The material of claim 14, wherein the coating or powder includes absorbed, trapped, or reacted atoms or molecules of oxygen.

18. The material of claim 17, wherein sufficient oxygen is incorporated in the coating or powder such that the particulate of the one or more antimicrobial metals during dissociation has a size less than 2 μm.

19. The material of claim 17, wherein sufficient oxygen is incorporated in the coating or powder such that the particulate of the one or more antimicrobial metals during dissociation has a size less than 1 μm.

20. The material of claim 18, wherein the one or more antimicrobial metals are silver, or an alloy or compound thereof, and wherein the coating or powder has a ratio of its temperature of recrystallization to its melting temperature, in degrees K ($T_{rec}/T_m$), less than 0.33.

21. The material of claim 20, wherein the ratio is less than 0.3.

22. The material of claim 21, wherein the temperature of recrystallization is less than about 140° C.

23. The material of claim 20, wherein the coating has a positive rest potential, when measured against a standard calomel electrode, in 0.15 M $Na_2CO_3$ or 0.15 M KOH.

24. The material of claim 23, wherein the positive rest potential is greater than 225 mV in 0.15 M $Na_2CO_3$.

25. The material of claim 23, wherein the positive rest potential is greater than 250 mV in 0.15 M $Na_2CO_3$.

26. The material of claim 23, wherein the bioabsorbable substrate is formed from a bioabsorbable polymer selected from:
   (a) polyester or polylactone selected from the group comprising polymers of polyglycolic acid, glycolide, lactic acid, lactide, dioxanone, trimethylene carbonate, polyanhydrides, polyesteramides, polyortheoesters, polyphosphazenes, and copolymers of these and related polymers or monomers;
   (b) protein, selected from the group comprising albumin, fibrin, collagen, or elastin;
   (c) polysaccharide, selected from the group comprising chitosan, alginates, or hyaluronic acid; or
   (d) biosynthetic polymer, comprising 3-hydroxybutyrate polymers.

27. The material of claim 23, wherein the bioabsorbable substrate is an alginate dressing coated with a coating of the one or more antimicrobial metals or impregnated with a powder of the one or more antimicrobial metals.

28. The material of claim 23, wherein the bioabsorbable substrate is a chitosan powder coated with a coating of the one or more antimicrobial metals.

* * * * *

UNITED STATES PATENT AND TRADEMARK OFFICE
CERTIFICATE OF CORRECTION

PATENT NO.     : 6,719,987 B2
DATED          : April 13, 2004
INVENTOR(S)    : Robert E. Burrell et al.

It is certified that error appears in the above-identified patent and that said Letters Patent is hereby corrected as shown below:

<u>Title page,</u>
Item [63], Related U.S. Application Data, "filed on Apr. 16, 2001." should be -- filed on Apr. 17, 2000. --

<u>Column 1,</u>
Line 7, "filed on Apr. 16, 2001." should be -- filed on Apr. 17, 2000. --

Signed and Sealed this

Eighteenth Day of January, 2005

JON W. DUDAS
*Director of the United States Patent and Trademark Office*